US00PP20111P2

(12) United States Plant Patent
Klemm

(10) Patent No.: US PP20,111 P2
(45) Date of Patent: Jun. 23, 2009

(54) *CALIBRACHOA* PLANT NAMED 'KLECA07154'

(50) Latin Name: ***Calibrachoa* hybrid**
Varietal Denomination: KLECA07154

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/080,399

(22) Filed: Apr. 2, 2008

(51) Int. Cl.
*A01H 5/00* (2006.01)

(52) U.S. Cl. ..... Plt./413

(58) Field of Classification Search ..... Plt./263, Plt./413
See application file for complete search history.

*Primary Examiner*—S. B. McCormick Ewoldt
(74) *Attorney, Agent, or Firm*—Jondle & Associates, P.C.

(57) ABSTRACT

A new *Calibrachoa* plant particularly distinguished by its orange-colored flowers, very high flower richness and its semi-upright plant habit is disclosed.

1 Drawing Sheet

Genus and species: *Calibrachoa* hybrid
Variety denomination: 'KLECA07154'.

BACKGROUND OF THE NEW PLANT

The present invention comprises a new and distinct cultivar of *Calibrachoa*, botanically known as *Calibrachoa* hybrid, and hereinafter referred to by the cultivar name 'KLECA07154'. The new cultivar originated from an open pollinization made in summer of 2004 in Stuttgart, Germany. The female parent was the dark-red-flowered proprietary *Calibrachoa* plant 'X 446' (unpatented), while the male parent was an unknown *Calibrachoa* plant.

The new cultivar was first propagated in May 2005 in Stuttgart, Germany and has been asexually reproduced by vegetative cuttings and tissue culture in Stuttgart, Germany over 35 generations. The present invention has been found to retain its distinctive characteristics through successive asexual propagations.

Plant Breeder's Rights for this cultivar were applied for in Canada on Apr. 5, 2007 and in Switzerland on Jul. 6, 2007. 'KLECA07154' has not been made publicly available more than one year prior to filing of this application.

SUMMARY OF THE INVENTION

The following are the most outstanding and distinguishing characteristics of this new cultivar when grown under normal horticultural practices in a greenhouse in Stuttgart, Germany.

1. Orange-colored flowers;
2. Very high floriferousness;
3. A semi-upright plant habit.

DESCRIPTION OF PHOTOGRAPH

This new *Calibrachoa* plant is illustrated by the accompanying photograph which shows overall plant habit including blooms, buds, and foliage of the plant; the colors shown are as true as can be reasonably obtained by conventional photographic procedures. The photograph is of a five-month-old *Calibrachoa* plant grown in a greenhouse in Stuttgart, Germany, between January and May 2007.

DESCRIPTION OF THE NEW CULTIVAR

The following detailed descriptions set forth the distinctive characteristics of 'KLECA07154'. The data which defines these characteristics were collected from asexual reproductions carried out in Stuttgart, Germany. The plant history was taken on five-month-old plants which were planted as rooted cuttings in 11-cm pots between January and May 2007 and then grown in a greenhouse. The plants had one terminal pinch one week after potting. Color readings were taken under natural light. Color references are primarily to the R.H.S. Colour Chart of The Royal Horticultural Society of London (R.H.S.) (2001).

DETAILED BOTANICAL DESCRIPTION OF THE NEW PLANT

Classification:
- *Family.*—Solanaceae.
- *Botanical.*—*Calibrachoa* hybrid.
- *Common name.*—*Calibrachoa*.

Parents:
- *Female.*—Dark-red-flowered proprietary *Calibrachoa* plant 'X 446' (unpatented).
- *Male.*—An unknown *Calibrachoa* plant.

Growth:
- *Form and habit.*—Semi-upright.
- *Height* (*measured from the top of the soil*).—16.0 cm.
- *Width* (*horizontal plant diameter*).—17.0 cm.
- *Time to produce a finished flowering plant.*—11 weeks.
- *Outdoor plant performance.*—High flower richness, healthy.
- *Time to initiate and develop roots.*—19 days.
- *Root description.*—Moderate density, freely branching, white roots.

Stems:
- *Length of basal branches.*—15.0 cm.
- *Internode length.*—1.0 cm to 3.0 cm.
- *Diameter of branches* (*from midpoint*).—2.0 cm to 6.0 cm.
- *Stem color.*—RHS 145A.
- *Texture.*—Smooth.

*Anthocyanin.*—Sometimes present as a red-brown color.

*Pedicel.*—Color: RHS 144B. Length: 1.6 cm. Diameter: 0.2 cm. Texture: Smooth.

Leaves:

*Arrangement.*—Alternate.

*Size.*—Length: 1.0 cm to 3.5 cm. Width: 0.5 cm to 2.0 cm.

*Shape.*—Lanceolate to elliptic.

*Apex.*—Broadly acute.

*Base.*—Attenuate.

*Margin.*—Entire.

*Color, both immature and mature.*—Upper surface: RHS 137A Lower surface: RHS 137C.

*Texture* (*both surfaces*).—Smooth.

*Venation.*—Pinnate.

*Venation color* (*both surfaces*).—RHS 144A.

*Petioles.*—Absent.

Flower bud:

*Shape.*—Irregular to oblong.

*Size.*—Length: 1.8 cm. Diameter: 0.4 cm.

*Color at tight bud.*—RHS 43D.

Inflorescence:

*Blooming habit.*—Continuous and rich flowering.

*Inflorescence type.*—Single.

*Floret type.*—Funnel-shaped.

*Lastingness of individual blooms on the plant.*—7 days.

*Fragrance.*—Absent.

Flowers:

*Immature flower.*—Diameter: Horizontal: 2.3 cm. Vertical: 2.3 cm. Color: Upper surface: RHS 43B. Lower surface: RHS 43D.

*Mature flower.*—Diameter: Horizontal: 2.5 cm. Vertical: 2.5 cm. Color: Upper surface: RHS 43B. Lower surface: RHS 43D.

*Corolla tube.*—Color inside: RHS 2C. Color outside: RHS 150C. Tube length: 1.5 cm. Outside texture: Smooth.

*Petals.*—Apex: Obverse. Base: Fused. Margin: Entire. Waviness of petals: Weak. Lobation: Weak. Texture (both surfaces): Smooth.

*Sepals.*—Calyx form: Rosette. Shape: Lanceolate to elliptic. Apex: Acute. Base: Fused. Margin: Entire. Length: 1.4 cm. Width: 0.3 cm. Color: Upper surface: RHS 138A. Lower surface: RHS 138B. Texture (both surfaces): Smooth.

Reproductive organs:

*Stamens.*—Number: 5. Filament color: RHS 154A. Filament length: 0.8 cm. Filament diameter: 0.1 cm. Pollen color: RHS 11A. Pollen quantity: Sparse.

*Pistils.*—Number: 1. Length: 0.2 cm. Diameter: 0.2 cm. Stigma color: RHS 149A. Style color: RHS 149A.

Fruit and seed set: No seed set observed.

Disease and insect resistance: No particular resistance or susceptibility has been observed.

COMPARISON WITH PARENTAL AND COMMERCIAL CULTIVARS

'KLECA07154' differs from the female parent 'X 446' (unpatented) by having an orange flower color, while 'X 446' has a dark-red flower color.

'KLECA07154' differs from the commercial cultivar 'MF Orange V 172' (unpatented) by having a darker and more intense orange flower color than 'MF Orange V 172'.

I claim:

1. A new and distinct cultivar of *Calibrachoa* plant as shown and described herein.

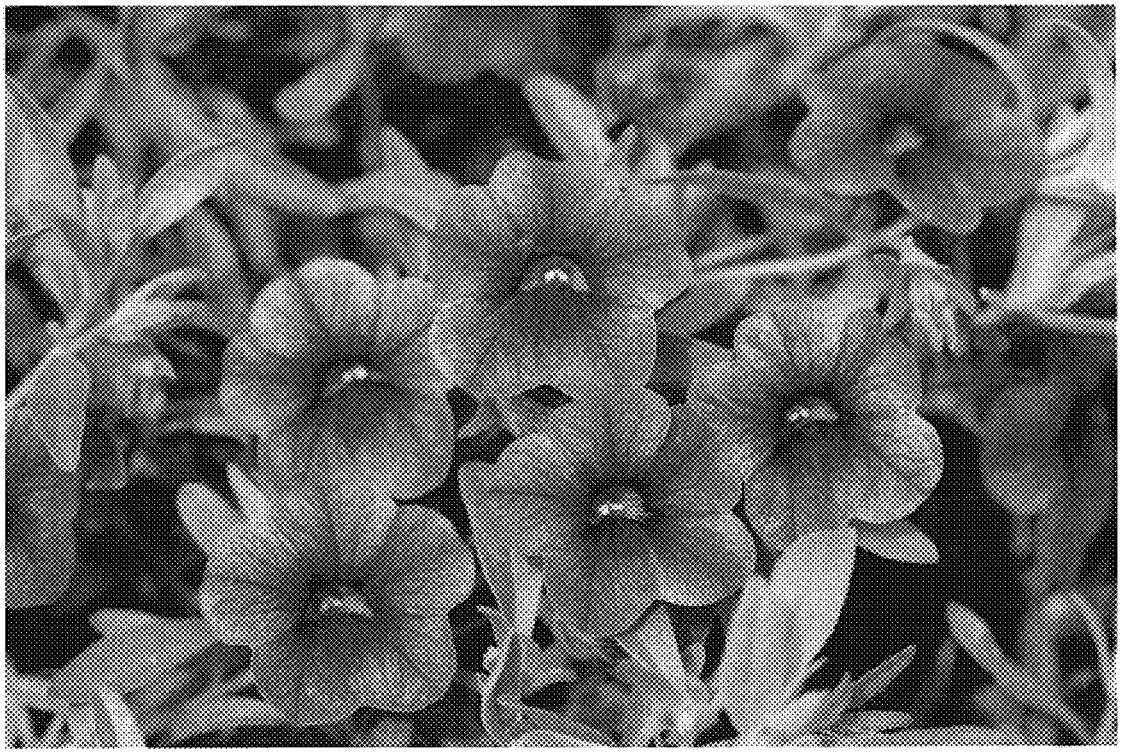

* * * * *